United States Patent [19]

Farr et al.

[11] 4,244,955

[45] Jan. 13, 1981

[54] 2,4A-ETHANOBENZ[G]ISOQUINOLIN-5(1H)-ONES AND THEIR USE AS ANTI-FERTILITY AND ANALGESIC AGENTS

[75] Inventors: Robert A. Farr; Joseph E. Dolfini, both of Cincinnati, Ohio

[73] Assignee: Richardson-Merrell Inc., Wilton, Conn.

[21] Appl. No.: 34,357

[22] Filed: Apr. 30, 1979

[51] Int. Cl.³ .................. A61K 31/435; C07D 221/18
[52] U.S. Cl. ...................................... 424/258; 546/72
[58] Field of Search .......................... 546/72; 424/258

[56] References Cited

PUBLICATIONS

Hollins, "Synthesis at Heterocyclic Nitrogen Compounds", (1924), pp. 390 & 391.

Primary Examiner—Donald G. Daus
Assistant Examiner—D. B. Springer
Attorney, Agent, or Firm—William J. Stein; Salvatore R. Conte

[57] ABSTRACT

2,4a-Ethanobenz[g]isoquinolin-5(1H)-one derivatives are described which are useful as analgesic and anti-fertility agents.

5 Claims, No Drawings

2,4A-ETHANOBENZ[G]ISOQUINOLIN-5(1H)-ONES AND THEIR USE AS ANTI-FERTILITY AND ANALGESIC AGENTS

DESCRIPTION

1. Technical Field

This invention relates to novel derivatives of 2,4a-ethanobenz[g]isoquinolin-5(1H)-ones useful for their analgesic and antifertility properties.

SUMMARY OF THE INVENTION

I have discovered that certain substituted 3-(phenylmethyl)-1-azabicyclo[2.2.2]octane-4-carboxylic acids when treated with an acidic dehydrating cyclizing agent result in the preparation of substituted 2,4a-ethanobenz[g]isoquinolin-5(1H)-ones that are useful as analgesic agents and antifertility agents. More particularly, these compounds are 2,4a-ethanobenz[g]isoquinolin-5(1H)-ones having the formula:

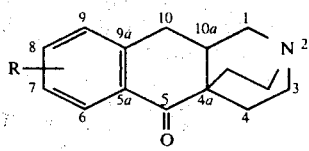

wherein R is selected from the group consisting of hydrogen, lower alkyl having from 1 to 4 carbon atoms and halogen, and the pharmaceutically acceptable salts thereof.

This invention further discloses a method whereby these derivatives are conveniently prepared. Additionally, this invention relates to the use of these compounds as analgesic and antifertility agents.

DETAILED DESCRIPTION OF THE INVENTION

As seen from general formula (I) above, all of the compounds of the present invention contain the tetracyclic nucleus 3,4,10,10a-tetrahydro-2,4a-ethanobenz[g]isoquinoline having a ketone in the 5-position. The only substitution present is at the terminal phenyl moiety of the molecule, the quinuclidine portion of the molecule remaining unsubstituted. For convenience of nomenclature, the compounds of this invention are hereinafter generally designated as derivatives of 2,4a-ethanobenz[g]isoquinolin-5(1H)-one.

Substitution of the phenyl moiety is illustrated by the symbol R at either the 6,7,8 or 9-position of the molecule. Where R is hydrogen, the unsubstituted parent species 3,4,10,10a-tetrahydro-2,4a-ethanobenz[g]isoquinolin-5(1H)-one is delineated. Additionally, the symbol R can represent a lower alkyl or halogen group.

The term lower alkyl is intended to include any monovalent radical derived from an aliphatic hydrocarbon having from 1 to 4 carbon atoms. Illustrative of such groups are the methyl, ethyl, propyl, isopropyl, butyl, isobutyl and t-butyl radicals. When the symbol R represents the lower alkyl group, a preferred class of compounds is designated within the broad scope of the invention. The term halogen, represented by the symbol R, is intended to include the usual non-metallic elements of fluorine, chlorine, bromine and iodine.

The pharmaceutically acceptable salts include the non-toxic organic or inorganic acid addition salts of the base compounds of formula (1) above. Illustrative inorganic acids which form suitable salts include hydrochloric, hydrobromic, sulfuric and phosphoric acids as well as the acid metal salts such as sodium monohydrogen orthophosphate and potassium hydrogen sulfate. Illustrative organic acids which form suitable salts include the mono, di and tricarboxylic acids, as for example, acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic and sulfonic acids such as methane sulfonic acid and 2-hydroxyethane sulfonic acid. Such salts can exist in either a hydrated or a substantially anhydrous form.

Illustrative specific base compounds that are encompassed by formula (1) above include:
6-methyl-3,4,10,10a-tetrahydro-2,4a-ethanobenz[g]isoquinolin-5(1H)-one,
9-chloro-3,4,10,10a-tetrahydro-2,4a-ethanobenz[g]isoquinolin-5(1H)-one,
8-ethyl-3,4,10,10a-tetrahydro-2,4a-ethanobenz[g]isoquinolin-5(1H)-one,
7-fluoro-3,4,10,10a-tetrahydro-2,4a-ethanobenz[g]isoquinolin-5(1H)-one,
9-isopropyl-3,4,10,10a-tetrahydro-2,4a-ethanobenz[g]isoquinolin-5(1H)-one,
6-t-butyl-3,4,10,10a-tetrahydro-2,4a-ethanobenz[g]isoquinolin-5(1H)-one,
6-bromo-3,4,10,10a-tetrahydro-2,4a-ethanobenz[g]isoquinolin-5(1H)-one,
8-iodo-3,4,10,10a-tetrahydro-2,4a-ethanobenz[g]isoquinolin-5(1H)-one,
7-propyl-3,4,10,10a-tetrahydro-2,4a-ethanobenz[g]isoquinolin-5(1H)-one, and
8-isobutyl-3,4,10,10a-tetrahydro-2,4a-ethanobenz[g]isoquinolin-5(1H)-one.

The products of this invention are prepared in good yield by reacting a 3-(phenylmethyl)-1-azabicyclo[2.2.2] octane-4-carboxylic acid with an acidic dehydrating cyclizing agent. This can be schematically indicated as follows wherein the symbol R represents the groups previously described.

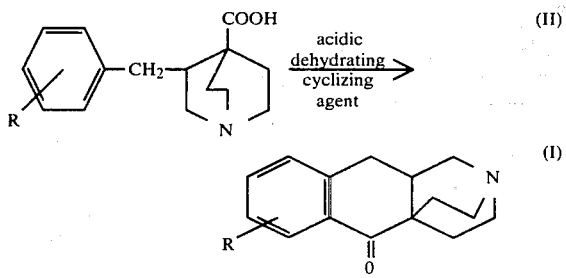

In general the cyclization is conducted by adding the substituted or unsubstituted 3-(phenylmethyl)-1-azabicyclo[2.2.2]octane-4-carboxylic acid to the acidic dehydrating cyclizing agent, permitting the carboxylic acid to undergo cyclization, and recovering the desired 2,4a-ethanobenz[g]isoquinolin-5(1H)-one from the reaction mixture. Suitable acidic dehydrating cyclizing agents that may be employed include polyphosphoric acid, sulfuric acid and trifluoroacetic anhydride, with polyphosphoric acid being the dehydrating agent of choice. The reaction can be conducted at a temperature range of from room temperature to about 150° C. for a period of time ranging from 1 to about 12 hours. Preferably, the carboxylic acid (II) above is added with stirring to a solution of polyphosphoric acid at a temperature of from 90° to 110° C. Stirring is continued for a period of from 2 to 4 hours in order to help dissipate the gaseous evolution that accompanies the reaction.

In general, the polyphosphoric and trifluoroacetic dehydrating agents are used neat. However, when sulfuric acid is employed as the dehydrating cyclizing agent, the reaction can be advantageously conducted in a suitable inert organic solvent in order to ameliorate and better control the reaction. Suitable solvents include chloroform or methylene chloride with chloroform being the solvent of choice.

The desired products so obtained are isolated and purified using standard isolation and purification techniques well known to those skilled in the art. Thus, for example, the reaction mixture is cooled, made basic with aqueous sodium hydroxide or potassium carbonate, and extracted with a suitable solvent, such as diethyl ether. The ether extracts can be combined, dried and concentrated to obtain the desired product. In some instances extraction of the reaction mixture using an ether/benzene solution is beneficial. The ether/benzene mixture serves not only to increase the solubility of the desired product, but also serves to free the product of any remaining traces of water via evaporation of the benzene-water azeotrope.

The 3-[(substituted-phenyl)methyl]-1-azabicyclo-[2.2.2]octane-4-carboxylic acids (II) employed as starting materials are readily obtained via the cyclization of the corresponding 1-[3-(substituted-phenyl)-2-propenyl]-4-piperidinecarbonitrile (III) by means of a strong base. Hydrolysis of the 3-[(substituted-phenyl)-methyl]-1-azabicyclo[2.2.2]octane-4-carbonitriles (IV) results in the formation of the 3-[(substituted-phenyl)-methyl]-1-azabicyclo[2.2.2]octane-4-carboxylic acids (II). This reaction can be schematically illustrated as follows:

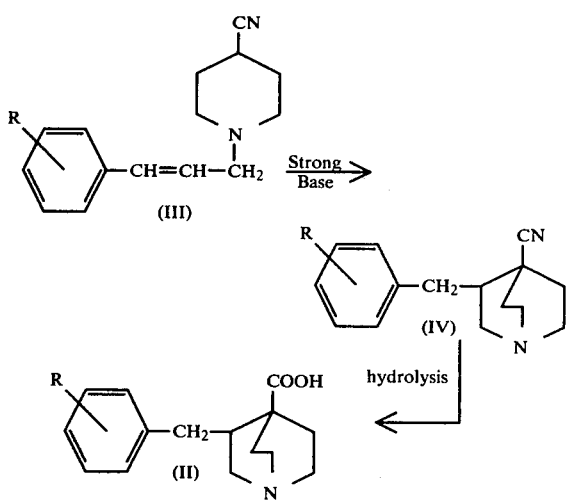

In general the cyclization of the 1-[(3-substituted-phenyl)-2-propenyl]-4-piperidinecarbonitrile (III) is conducted in the presence of a strong base, as for example, the alkyl or dialkyl amides of alkali metals. Either the sodium, lithium or potassium alkylamides are favorably employed. The amides may be either N-alkyl-substituted or N,N-dialkyl-substituted in which the alkyl group is an unbranched lower alkyl group having from 1 to 4 carbon atoms. Preferably, the lithium dialkylamides are employed in which the alkyl group is either a methyl or ethyl radical. Approximately one equivalent (or a slight excess thereof) is required for the strong base, calculated on the basis of the starting material. Preferably, the base of choice is a freshly prepared solution of lithium diethylamide.

The 1-[(3-substituted-phenyl)-2-propenyl]-4-piperidinecarbonitrile (III) is caused to react in an inert, anhydrous organic solvent which does not interfere with the reaction. Various inert solvents that can be employed include dimethoxyethane, dioxane, tetrahydrofuran, benzene, ether and other related reaction media. The solvent preferably employed is tetrahydrofuran.

The reaction is conducted at temperatures ranging from −25° C. to 60° C. for a period of from 15 minutes to 4 hours or until the maximum amount of 3-[(substituted-phenyl)methyl]-1-azabicyclo[2.2.2]actane-4-carbonitrile (IV) is obtained. Preferably the reaction is initially conducted at −20° C. and then warmed rapidly to 50°–55° C. under continuous stirring. The reaction mixture is quenched by dilution in water and the desired product is isolated using techniques well known to those skilled in the art. Thus, for example, the quenched reaction mixture can be extracted with an organic solvent, as for example chloroform, methylene chloride or ether, the combined organic extracts dried and evaporated in vacuo and the residue purified by crystallization from a suitable organic solvent or solvent mixture.

Hydrolysis of the 3-[(substituted-phenyl)methyl]-1-azabicyclo[2.2.2]octane-4-carbonitrile (IV) so obtained is readily conducted in aqueous alkali or acid. Preferably, hydrolysis is conducted via an aqueous solution of a strong mineral acid, such as hydrochloric or sulfuric acid, in order to facilitate the isolation of the 3-[(substituted-phenyl)methyl]-1-azabicyclo[2.2.2]-octane-4-carboxylic acids (II). Thus, the particular 3-[(substituted-phenyl)methyl]-1-azabicyclo[2.2.2]octane-4-carbonitrile (IV) can be stirred in a solution of 6N hydrochloric acid at its reflux temperature for a period of about 24 hours. Upon cooling the desired 3-[(substituted-phenyl)methyl]-1-azabicyclo[2.2.2]octane-4-carboxylic acid (II) crystallizes from the hydrolysis medium as the free hydrochloride salt.

The compounds of formula I possess useful analgesic properties for the amelioration of pain in warm-blooded animals when administered at a dosage of about 0.5 to 150 mg/kg per day. The preferred dosage range is usually from about 2 to 10 mg/kg per day. In terms of drug dosage for internal administration, a dose of from about 5 to about 500 mg of therapeutic component per dosage unit can be administered at intervals of one or several times per day. Preferably, a dosage unit containing from 50 to 200 mg of active ingredient is employed.

Additionally, the compounds of this invention possess antifertility activity in warm-blooded animals. This can be demonstrated by the effects of these compounds upon nidation and implantation when administered to pregnant hamsters at a point immediate and subsequent to nidation and observing their prepartum effects. The particular dosage of the active ingredient employed depends upon such factors as the route of administration, age, weight of the mammal being treated and the frequency of dosing. In general, the compounds can be administered to warm-blooded animals at a dosage of about 0.5 to about 150 mg/kg per day. A dosage of 20 mg to 50 mg/kg per day is preferably employed.

A post-ovulatory dosage unit of the therapeutic agent contains from about 0.1 mg to about 3.0 g of the active ingredient per administration with dosages repeated as necessary. Dosage units administered prior to ovulation can contain from about 5 mg to about 500 mg depending upon the particular compound employed. Preferably a dosage unit containing from 20 mg to 100 mg of active ingredient is employed. The actual amount required varies from compound to compound but is an amount in humans that is sufficient to prevent nidation from occurring and that will produce menstrual bleeding in fertile female humans. In the case of a subcutaneous, depot preparation or medicated intrauterine device, amounts of up to 3.0 grams of the active ingredient can be administered once or twice a year.

Illustrative of the term "warm-blooded animals" are such species as mice, rats, guinea pigs, hamsters, rabbits, dogs, cats, cows, horses and primates including monkeys, baboons and humans.

The 2,4a-ethanobenz[g]isoquinolin-5(1H)-ones (I) of this invention are generally administered in the form of their pharmaceutically acceptable salts, in combination with a pharmaceutical carrier using various conventional dosage unit forms. Thus, the compounds of the present invention are administered in various dosage unit forms such as tablets, capsules, powders, granules, oral solutions or suspensions, sterile solutions or suspensions for parenteral use, sublingual and intrabuccal preparations, aerosols and sprays for inhalation and insufflation therapy, creams, lotions, and ointments for topical use, intravaginal and rectal suppositories, vaginal rings impregnated with the active ingredient, intrauterine devices, subcutaneous and intramuscular implants, depot preparations and as further illustrated in the Examples.

In the preparation of solid compositions such as tablets, the principal active ingredient is mixed with conventional pharmaceutical excipients such as gelatin, starches, lactose, magnesium stearate, talc, acacia, dicalcium phosphate and functionally similar materials. Tablets can be laminated, coated or otherwise compounded to provide for a prolonged or delayed action or to release a predetermined successive amount of medication. Capsules are prepared by mixing the active ingredient with an inert pharmaceutical filler or diluent and filling in either hard gelatin capsules or machine encapsulated soft gelatin capsules. Syrups or elixirs can contain the active ingredients together with sucrose or other sweetening agents, methyl and propyl parabens as preservatives, and suitable color and flavoring agents.

Parenteral fluid dosage forms are prepared by utilizing the active ingredient in a sterile liquid vehicle, the preferred vehicle being water or a saline solution. The parenteral formulations include those administerable by a jet gun. Compositions having the desired clarity, stability and adaptability for parenteral use are obtained by dissolving from about 0.1 mg to about 3 grams of the active ingredient in a vehicle consisting of a mixture of nonvolatile, liquid polyethylene glycols, which are soluble in water and organic liquids, and which have molecular weight ranging from about 200 to about 1500. The solutions may advantageously contain suspending agents, such as sodium carboxymethylcellulose, methylcellulose, polyvinylpyrrolidone or polyvinyl alcohol. Additionally, they may contain bactericidal and fungicidal agents, as for example, parabens, benzyl alcohol, phenol or thimerosal. If desired, isotonic agents can be included such as dextrose or sodium chloride, as well as local anesthetics, stabilizing or buffering agents. In order to further enhance stability, the parenteral compositions may be frozen after filling and water removed by freeze-drying techniques well known in the art. Such dry, lyophilized powders are generally reconstituted immediately prior to use.

Topical ointments are prepared by dispensing the active ingredient in a suitable ointment base such as petrolatum, lanolin, polyethylene glycols or mixtures thereof. Generally, the steroid is finely divided by milling or grinding. Creams and lotions are prepared by dispersing the active ingredient in an oily phase and subsequently forming an emulsion thereof.

The active ingredient can also be compressed into pellets and implanted subcutaneously or intramuscularly as a depot injection or implant. Implantation results in a slow but predetermined rate of absorption from the site of implantation. Such implants may additionally employ inert materials, as for example, biodegradable polymers and synthetic silicone polymer rubbers.

The instant compounds can also be mixed with a silicone polymer and molded in the form of cylindrical rings, loops, coils, petals or other shapes which can be inserted directly into the uterus. The active ingredient diffuses through the permeable polymeric material at a relatively slow and constant rate thereby enabling its antiprogestational effects to be available directly at the site of severe activity.

The following preparation and examples are illustrative of the novel compounds of the present invention, their preparation, compositions and use in accordance with the above.

EXAMPLE 1

1-(3-Phenyl-2-propenyl)-4-piperidinecarbonitrile

A mixture of 60.0 g of isonipecotamide (4-piperidinecarboxamide), 75.0 g of (3-chloropropenyl)-benzene and 72 g of potassium acid carbonate suspended in 700 ml of toluene are heated with stirring at their reflux temperature for a period of 4 hours. The reaction mixture is cooled, water added thereto and filtered. The crude product is washed with water, ether and recrystallized from a 5:1 ethanol/water mixture to yield 99.4 g of 1-(3-phenyl-2-propenyl)-4-piperidinecarboxamide as light beige needles having a m.pt. of 189.5°–191.5° C.

A mixture of 99.4 g of the 1-(3-phenyl-2-propenyl)-4-piperidinecarboxamide, 25 ml of phosphorus oxychloride and 30 g of sodium chloride are suspended in 750 ml of 1,2-dichloroethane and heated to its reflux temperature with vigorous stirring for a period of 2 hours. After several minutes at the reflux temperature a white precipitate separates. The reaction mixture is cooled, a 10% sodium hydroxide solution is added and the mixture extracted with diethyl ether. The combined extracts are washed with water, followed by a solution of sodium chloride, dried (MgSO$_4$) and concentrated in vacuo. The residual oil is distilled under reduced pressure to yield the desired 1-(3-phenyl-2-propenyl)-4-piperidinecarbonitrile as a viscous, colorless oil, b.p. 169°–76° C./0.35–0.70 mm.

EXAMPLE 2

3-(Phenylmethyl)-1-azabicyclo[2.2.2]octane-4-carbonitrile

To a solution of 18.6 ml of 2.45 M n-butyllithium in hexane at 0° C. under an atmosphere of argon is added a solution of 20 ml of diethylamine (dried over 3 Å molecular sieves) in 150 ml of tetrahydrofuran, that has been freshly distilled from calcium hydride. The mixture is stirred for a period of about 15 minutes, whereupon a solution of 10.0 g of 1-(3-phenyl-2-propenyl)-4-piperidinecarbonitrile dissolved in 50 ml of dry tetrahydrofuran is added via dropwise addition over a period of about 20 minutes. The reaction mixture is stirred for an additional 10 minutes at 0° C., heated to 50°–55° C. for about 20 minutes, cooled and quenched by the addition of water. The resulting mixture is extracted with ether. The combined extracts are washed once with water and extracted twice with a dilute hydrochloric acid solution. The hydrochloric acid extracts are washed with ether and the aqueous layer made alkaline using a cold aqueous sodium hydroxide solution. This alkaline solution is extracted with ether and the combined ether extracts are dried (MgSO$_4$) and concentrated in vacuo to yield 8.7 g of an orange oil. The oil is passed through a short alumina column and eluted with methylene chloride. Concentration of the eluate affords 7.1 g of yellow crystalline material, which upon recrystallization from cyclohexane yields 3.67 g of 3-(phenylmethyl)-1-azabicyclo[2.2.2]octane-4-carbonitrile as colorless crystals having a m.pt. of 82.5°–84° C.

EXAMPLE 3

3-(Phenylmethyl)-1-azabicyclo[2.2.2]octane-4-carboxylic acid

The compound 3-(phenylmethyl)-1-azabicyclo[2.2.2]-octane-4-carbonitrile, prepared in accordance with the preceding Example, is dissolved in 10 ml of a 6N aqueous hydrochloric acid solution with stirring and the reaction mixture is maintained at its reflux temperature for 24 hours and permitted to slowly cool. The reaction mixture is cooled overnight at 0° C. and the crystals which form are removed by filtration and washed with ice-cold HCl and ether. Recrystallization from a 50:50 mixture of methanol/butanone provides fine white star clusters of 3-(phenylmethyl)-1-azabicyclo[2.2.2]octane-4-carboxylic acid hydrochloride having a m.pt. of 341°–4° C. (dec.).

EXAMPLE 4

3,4,10,10a-Tetrahydro-2,4a-ethanobenz[g]-isoquinolin-5(1H)-one

To a solution of 107 g of polyphosphoric acid maintained at 100° C., is added in small portions with stirring 8.6 g of 3-(phenylmethyl)-1-azabicyclo[2.2.2]-octane-4-carboxylic acid, prepared in accordance with the preceding Example. The reaction, which is accompanied by gaseous evolution, is stirred at 120° C. for approximately 3 hours and cooled. The reaction mixture is diluted with ice, made strongly basic with a solution of sodium hydroxide and extracted with a diethyl ether/benzene mixture. The combined extracts are dried and evaporated in vacuo. The residuel solid is dissolved in alcohol and either concentrated hydrochloric acid or alcoholic hydrochloric acid is added to convert it to the hydrochloride salt. The mixture is evaporated in vacuo and the residue recrystallized from a methanol/butanone mixture to yield 5.5 g of 3,4,10,10a-tetrahydro-2,4a-ethanobenz[g]isoquinolin-5(1H)-one hydrochloride as fine white needles having a m.pt. greater than 350° C.

Following essentially the same procedure but substituting 3-[(o-methylphenyl)methyl]-1-azabicyclo[2.2.2]-octane-4-carboxylic acid, 3-[(p-bromophenyl)methyl]-1-azabicyclo[2.2.2]octane-4-carboxylic acid, 3-[(m-isopropylphenyl)methyl]-1-azabicyclo[2.2.2]octane-4-carboxylic acid, and 3-[(o-chlorophenyl)methyl]-1-azabicyclo[2.2.2]octane-4-carboxylic acid for the 3-(phenylmethyl)-1-azabicyclo[2.2.2]octane-4-carboxylic acid above results in the formation of 9-methyl-3,4,10,10a-tetrahydro-2,4a-ethanobenz[g]isoquinolin-5(1H)-one, 7-bromo-3,4,10,10a-tetrahydro-2,4a-ethanobenz[g]isoquinolin-5(1H)-one, 8-isopropyl-3,4,10,10a-tetrahydro-2,4a-ethanobenz[g]isoquinolin-5(1H)-one, and 9-chloro-3,4,10,10a-tetrahydro-2,4a-ethanobenz[g]isoquinolin-5(1H)-one as their hydrochloride salts, respectively.

EXAMPLE 5

Preparation of a Tablet Formulation

An illustrative composition for tablets is as follows:

|  | Per Tablet |
|---|---|
| (a) 3,4,10,10a-tetrahydro-2,4a-ethanobenz[g]isoquinolin-5(1H)-one | 200 mg |
| (b) Wheat starch | 15 mg |
| (c) Lactose | 83.5 mg |
| (d) Magnesium stearate | 1.5 mg |

The granulation obtained upon mixing lactose, starch and granulated starch paste is dried, screened and mixed with the active ingredient and magnesium stearate. The mixture is compressed into tablets weighing 300 milligrams each.

EXAMPLE 6

Preparation of a Capsule Formulation

An illustrative composition for hard gelatin capsules is as follows:

|  | Per Tablet |
|---|---|
| (a) 8-ethyl-3,4,10,10a-tetrahydro-2,4a-ethanobenz[g]isoquinolin-5(1H)-one | 200 mg |
| (b) Talc | 35 mg |

The formulation is prepared by passing the dry powders of both (a) and (b) through a fine mesh screen and mixing them well. The powder is then filled into No. 0 hard gelatin capsules at a net fill of 235 mg per capsule.

In a similar fashion, a soft gelatin capsule is prepared in which the talc is omitted. The dry 8-ethyl-3,4,10,10a-tetrahydro-2,4a-ethanobenz[g]isoquinolin-5(1H)-one powder can be filled directly as a granulation, slug or compressed tablet into a rotary dye or plate mold in which the soft gelatin capsule is formed.

EXAMPLE 7

Preparation of Parenteral Formulation

An illustrative composition for a parenteral injection is the following emulsion:

| Each ml contains | Ingredients | Amount |
|---|---|---|
| 50 mg | 6-chloro-3,4,10,10a-tetra-hydro-2,4a-ethanobenz[g]-isoquinolin-5(1H)-one | 1.000 g |
| 100 mg | Polyoxyethylene sorbitan monooleate | 2.000 g |
| 64 mg | Sodium chloride | 0.128 g |
|  | Water for injection, q.s. | 20.000 ml |

The parenteral composition is prepared by dissolving 0.64 g of sodium chloride in 100 ml of water for injection, mixing the polyoxyethylene sorbitan monooleate with the 6-chloro-3,4,10,10a-tetrahydro-2,4a-ethanobenz[g]isoquinolin-5(1H)-one, adding a sufficient solution of the sodium chloride in water to the active ingredient and polyoxyethylene sorbitan monooleate to bring the volume to 20 ml, shaking the mixture, and finally autoclaving the mixture for 20 minutes at 110° C., at 15 p.s.i.g. steam pressure. The composition can be dispensed either in a single ampule for subsequent use in multiple dosage or in groups of 10 and 20 ampules for a single dosage administration.

EXAMPLE 8

Analgesic Activity

A group of 4 commercially available male mice (Chas. River strain, weight range 18–26 grams) are administered the test compound. After a period of 30 minutes 0.4 cc of an aqueous 0.25% of glacial acetic acid is intraperitoneally administered to each mouse. Starting 5 minutes following the acetic acid injection, the mice are continuously observed for any writhing or squirming episodes that characteristically take place. Those mice in which no episodes of writhing or squirming are observed during a 15 minute observation period are considered protected due to the analgesic action of the test compound.

Using this test system, the compound 3,4,10,10a-tetrahydro-2,4a-ethanobenz[g]isoquinolin-5(1H)-one hydrochloride, when subcutaneously administered at a dosage of 5 mg/kg completely protects three out of four mice from any writhing or squirming episodes.

EXAMPLE 9

Antifertility Activity

Commercially available female hamsters are mated and made pregnant by cohabitating with males overnight. Vaginal smears are taken on the following morning to see if they are sperm positive. A positive smear indicates day one of pregnancy. Test animals are placed in groups of eight with two to three animals per cage under conditions which enable a control of temperature, humidity, air-flow, feed and water. The test group of animals are treated on days 3, 4, 5, 6, 7 and 8 of pregnancy with the test compound by subcutaneous administration. This period of treatment in the hamster roughly corresponds in the fertile human female from a point just prior to implantation to a point subsequent to the ovarianplacental shift, i.e., the point at which placental circulation is complete.

Treatment in vehicle only control groups are sacrificed on day 15 of pregnancy. At necropsy each animal is classified with live feti, as not pregnant with resorbed uterine implantation sites, or as not pregnant with no evidence of conception having taken place. The antifertility activity is indicated by a decrease in the total number of live feti in the treatment group as compared to those in the vehicle control group.

Using this test system, the compound 3,4,10,10a-tetrahydro-2,4a-ethanobenz[g]isoquinolin-5(1H)-one hydrochloride when administered subcutaneously at a dosage leel of 30.0 mg/kg during the period of days 3 through 8 of pregnancy, exhibits an antifertility activity with 23 live feti for 5 animals present at day 15, one day prior to parturition. In contrast thereto, the control group of 8 animals receiving a placebo results in 100 live feti at day 15.

We claim:

1. A 2,4a-ethanobenz[g]isoquinolin-5(1H)-one having the formula

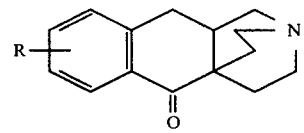

wherein R is selected from the group consisting of hydrogen, lower alkyl having from 1 to 4 carbon atoms and halogen, and the pharmaceutically acceptable salts thereof.

2. A compound according to claim 1 wherein R is lower alkyl having from 1 to 4 carbon atoms.

3. A compound of claim 1 which is 3,4,10,10a-tetrahydro-2,4a-ethanobenz[g]isoquinolin-5(1H)-one hydrochloride.

4. An analgesic composition in dosage unit form comprising an analgesic effective amount of from 5 to 500 mg of a compound of claim 1 in association with a pharmaceutical carrier.

5. An antifertility composition in dosage unit form comprising an anti-fertility effective amount of from 5 to 500 mg of a compound of claim 1 in association with a pharmaceutical carrier.

* * * * *